United States Patent
Pelagatti

(10) Patent No.: US 6,269,720 B1
(45) Date of Patent: Aug. 7, 2001

(54) DEVICE FOR CUTTING LAMINAR ELEMENTS TO LENGTH, FOR THE FABRICATION OF HYGIENIC AND SANITARY ARTICLES FOR EXAMPLE

(75) Inventor: Pietro Pelagatti, Chieti (IT)

(73) Assignee: Fameccanica.Data S.p.A., Chieti (IT)

( * ) Notice: Subject to any disclaimer, the term of this patent is extended or adjusted under 35 U.S.C. 154(b) by 0 days.

(21) Appl. No.: 09/270,838

(22) Filed: Mar. 18, 1999

(30) Foreign Application Priority Data

Mar. 19, 1998 (EP) .................................................. 98830154

(51) Int. Cl.[7] ................. B26D 1/62; B26D 5/08
(52) U.S. Cl. ................. 83/343; 83/76; 83/76.8; 83/100; 83/110; 83/113; 83/152; 83/155; 83/369
(58) Field of Search ..................... 156/353, 495, 156/494, 521, 256; 83/76, 402, 100, 110, 112, 113, 155, 152, 349, 76.8, 360, 369, 303, 324, 334, 343

(56) References Cited

U.S. PATENT DOCUMENTS

| 3,399,587 | 9/1968 | Lee et al. ................................ 83/99 |
| 3,728,191 | 4/1973 | Wierzba et al. ..................... 156/265 |
| 3,772,120 | 11/1973 | Radzins ............................... 156/264 |
| 3,898,900 | * 8/1975 | Schmermund ......................... 83/152 |
| 3,899,385 | * 8/1975 | Brinkmeier ......................... 156/521 |
| 3,963,557 | 6/1976 | Patterson ............................... 156/519 |
| 4,544,431 | * 10/1985 | King ..................................... 156/256 |
| 5,024,128 | * 6/1991 | Campbell, Jr. .................... 83/110 X |
| 5,399,216 | * 3/1995 | Galchefsi et al. ................. 156/215 |

FOREIGN PATENT DOCUMENTS

| 2853033 | 6/1980 | (DE) . |
| 0141338 | 5/1985 | (EP) . |

* cited by examiner

Primary Examiner—Boyer Ashley
(74) Attorney, Agent, or Firm—Roylance, Abrams, Berdo & Goodman, L.L.P.

(57) ABSTRACT

Laminated elements, which may be constituted, for example, by labels to be applied to articles while in movement, are formed from a strip provided by a feeding device. The strip moves forward onto a reception unit, passing through a cutting zone. The individual laminated elements are formed by causing the cutting unit to come into action when the length of the strip paid out by the feeding unit is equal to the desired length of the labels. The cutting unit preferably includes a revolving knife and a counterknife, where the latter consists of a non-driven roller supported in a cradle that is lubricated and exerts an elastic force against the cutting unit. Preferably, the reception unit realizes the step of applying the individual laminated elements to their respective articles.

22 Claims, 3 Drawing Sheets

DEVICE FOR CUTTING LAMINAR ELEMENTS TO LENGTH, FOR THE FABRICATION OF HYGIENIC AND SANITARY ARTICLES FOR EXAMPLE

BACKGROUND OF THE INVENTION

The present invention relates to a device intended for cutting laminar elements to their proper length. The invention has been developed with particular attention paid to its possible use in the field of plants for the fabrication of such hygienic and sanitary products as sanitary towels, nappies, baby diapers, etc.

On the basis of one of the solutions that is very widely used today, these products are fabricated in continuous or "in line" processes, that is to say, starting from a plurality of strips or webs that are superposed and paired in various ways to obtain a final strip or web from which the individual final products can then be obtained (generally by means of a cutting operation).

In the course of the various phases of the aforesaid fabrication process—and even in the phases that follow the obtainment of the individual final products—there may arise the need for applying to a moving element (quite irrespective of whether this element is of the continuous type or forms part of a continuous or substantially continuous flow of distinct elements) some laminar elements that, with a view to that application, have to be cut to length. As a general rule, the cutting operation is realized in a phased manner, because it is intended to generate elements capable of being applied at a predetermined rhythm (and, more often than not, in keeping with a given "phasing") related to the output flow rate.

The satisfaction of these needs is rendered more critical by the fact that most of the time the laminar elements in question have to have a length that is different from the length of the articles to which they have to be applied (as a general rule, they have to be "shorter").

For example, the laminar element that has to be cut to length may be the absorbing core or pad of a hygienic or sanitary product that has an overall length greater than that of the absorption pad it contains: to render the idea a little clearer, one needs only think of the distance that separates the two waist lines of a normal pair of nappies or diapers, a distance that is usually greater than that of the anteroposterior length of the absorption pad. Another example of a laminar element that may have to be cut to length before being applied in a rhythmic manner to a flow of articles is constituted by the label or labels (which are generally made of siliconized paper) that have to be applied to the zones of a hygienic or sanitary article treated with adhesive material. As a typical example, the present description will henceforth make reference to ladies' sanitary towels of the type generally known as "winged". In this case the finished product has three zones that have been treated with adhesives: one of these extends along the principal median axis of the towel and permits it to be accurately positioned in the crotch portion of the slip of the wearer, while the other two, which are of shorter length, are situated on the wings to permit the bent-back wings to adhere to a position below the crotch portion of the slip. In all three cases the adhesive-protection label has a length shorter than the overall length of the product (and, in the case of the labels to be applied to the wings, also much shorter). There is thus need for arranging things in such a way that the labels can be i) cut to the desired length and ii) accurately applied in the position of the adhesive zone that the label is to protect.

The machines used at present to satisfy these needs are based on a configuration that can be defined as a transfer; after being fed to the machine in the form of a strip, the material of which the labels are made is first subjected to a cutting operation by means of a head provided with revolving knives acting on a receiving counter-roller that subsequently also undertakes the actual application of the labels to the articles as they move forward.

When a given production line is expected to be used for the realization of either different products or the same product in different formats, so that there is need to have available elements cut into different lengths, it becomes necessary to use cutting and/or application devices of different types that have to be appropriately substituted for each other in order to obtain products having the desired characteristics. All this becomes translated into a greater global cost of the plant and, above all, the need of shutting down the plant, sometimes for rather long periods of time, whenever one has to pass to the production of an article having characteristics different from the article of the previous production run (the so-called "format changes").

SUMMARY OF THE INVENTION

The present invention sets out to realize a cutting device that can be used, among others, in the application context just discussed, though without giving rise to any of the previously mentioned difficulties associated therewith. According to the present invention, in fact, this scope can be realized by means of a device having the characteristics specifically set out in the claims attached hereto.

The indication of the fact that the solution in accordance with the invention is intended—among others—to be employed in the application context explicitly referred to in the preceding remarks should not be taken to mean that the invention is limited to the application context for which it was specifically developed. In fact, the invention is suitable for being applied quite generally in all the contexts in which there exists the need for realizing a rhythmic or phased cutting to length of laminated elements as a preliminary to their subsequent application to a strip and/or a continuous or substantially continuous flow of moving articles.

To all intents and purposes the solution according to the invention is based on the idea of relieving the element that is traditionally used to cooperate with the knife or the knives in the cutting operation (the so-called counterknife) of the additional task of assuring the rhythmic transfer of the elements obtained by means of the cutting operation. In what is at present the preferred embodiment form of the invention, in particular, a non-driven roller of elongated and slender shape and a very small diameter (diameter of the order of 12 mm) is used as counterknife; immediately downstream of the counter-roller there is situated a transfer belt operated by the principal driving unit of the plant for the transfer of the articles: it is thus possible for the speed to be brought automatically into line with the flow rate of the articles. Preferably, moreover, the counterknife is mounted in a special lubricated cradle, subjected to elastic loads and capable of adequately distributing the shear stress.

BRIEF DESCRIPTION OF THE DRAWINGS

The invention will now be described, though only as an example not to be considered as limitative in any manner or wise, by reference to the drawings attached hereto, where.

DETAILED DESCRIPTION OF THE PREFERRED EMBODIMENT

In Figure the reference number 1 indicates the whole of a device that can be used for cutting laminar elements to length and subsequently applying them within the ambit of a plant for the fabrication of hygienic and sanitary products. In the application example illustrated—and it is indeed just one such example—the articles or products in question are constituted by sanitary towels A.

In particular, FIG. 1 relates to a solution in which the articles A move forward in a continuous flow (for example, because they are still attached to each other in the form of a strip or a web) on a conveyor C, which may be—for example—of the motor-operated belt type, situated in a position below the device 1.

Figure 1:
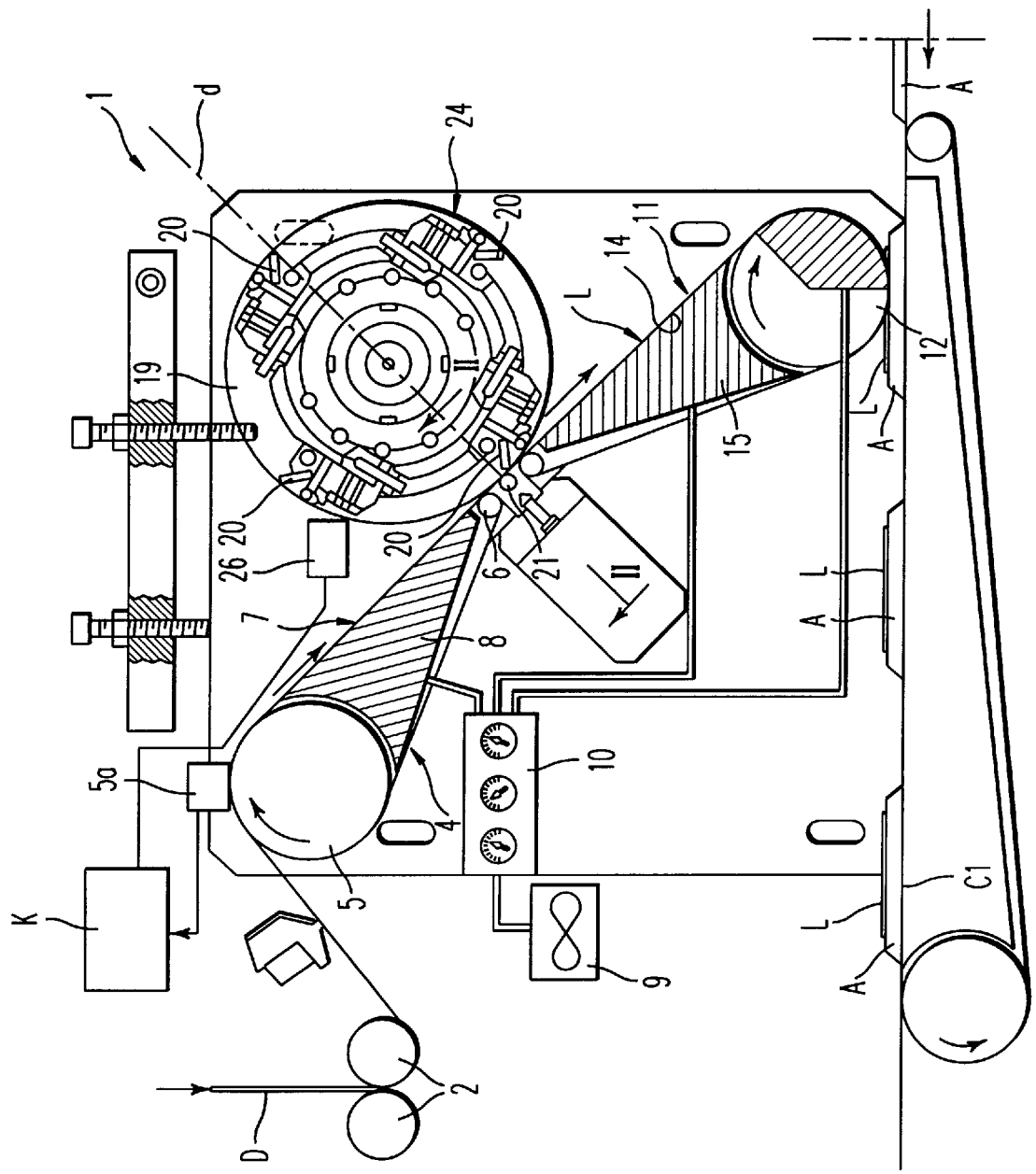
FIG. 1 shows a general view of the device according to the invention in side elevation.
Figure 2:
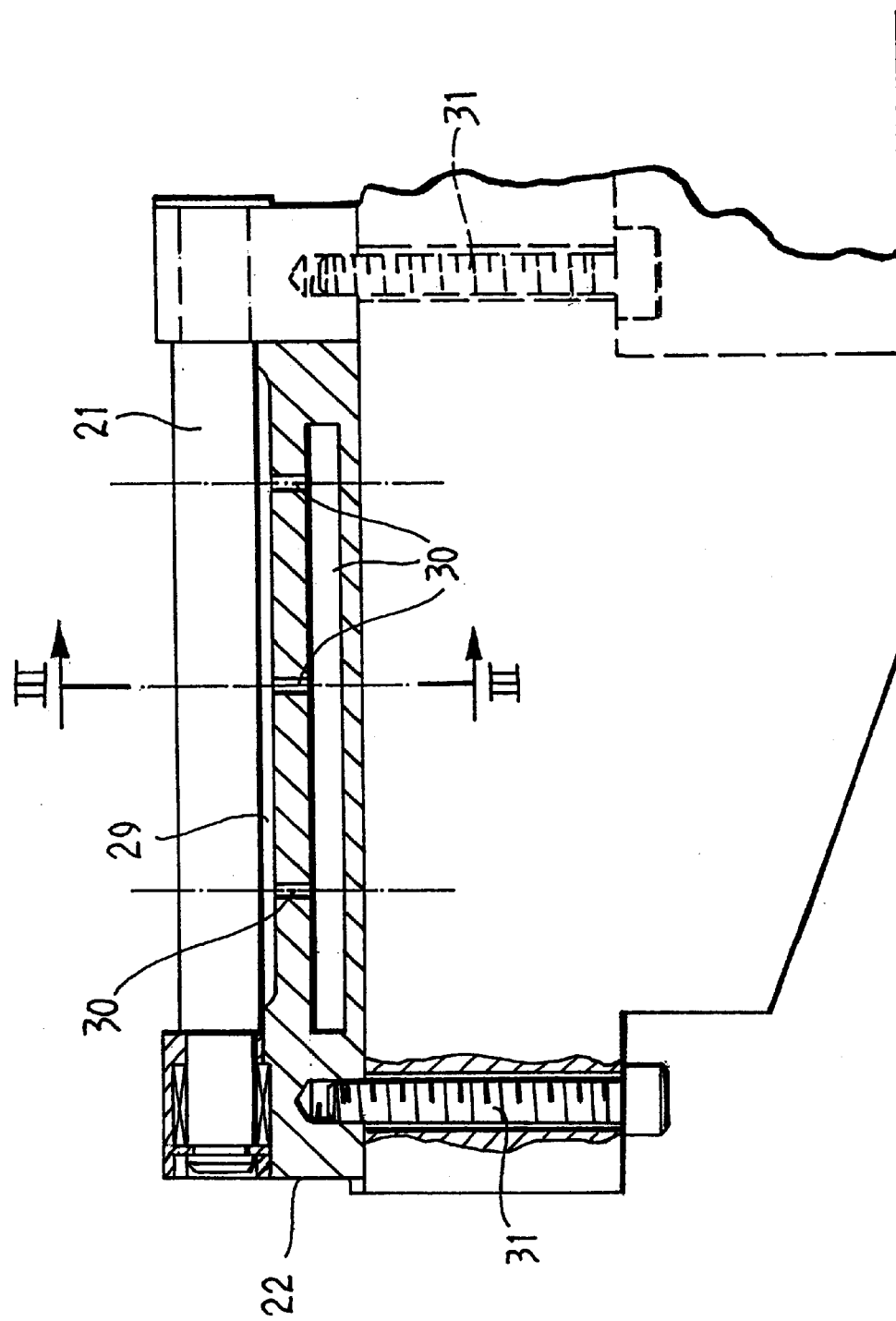
FIG. 2 shows a section through the device in accordance with the invention along the line II—II of FIG. 1, and FIG. 3 substantially shows a section through the device in accordance with the invention along the line III—III of FIG. 2.
Figure 3:
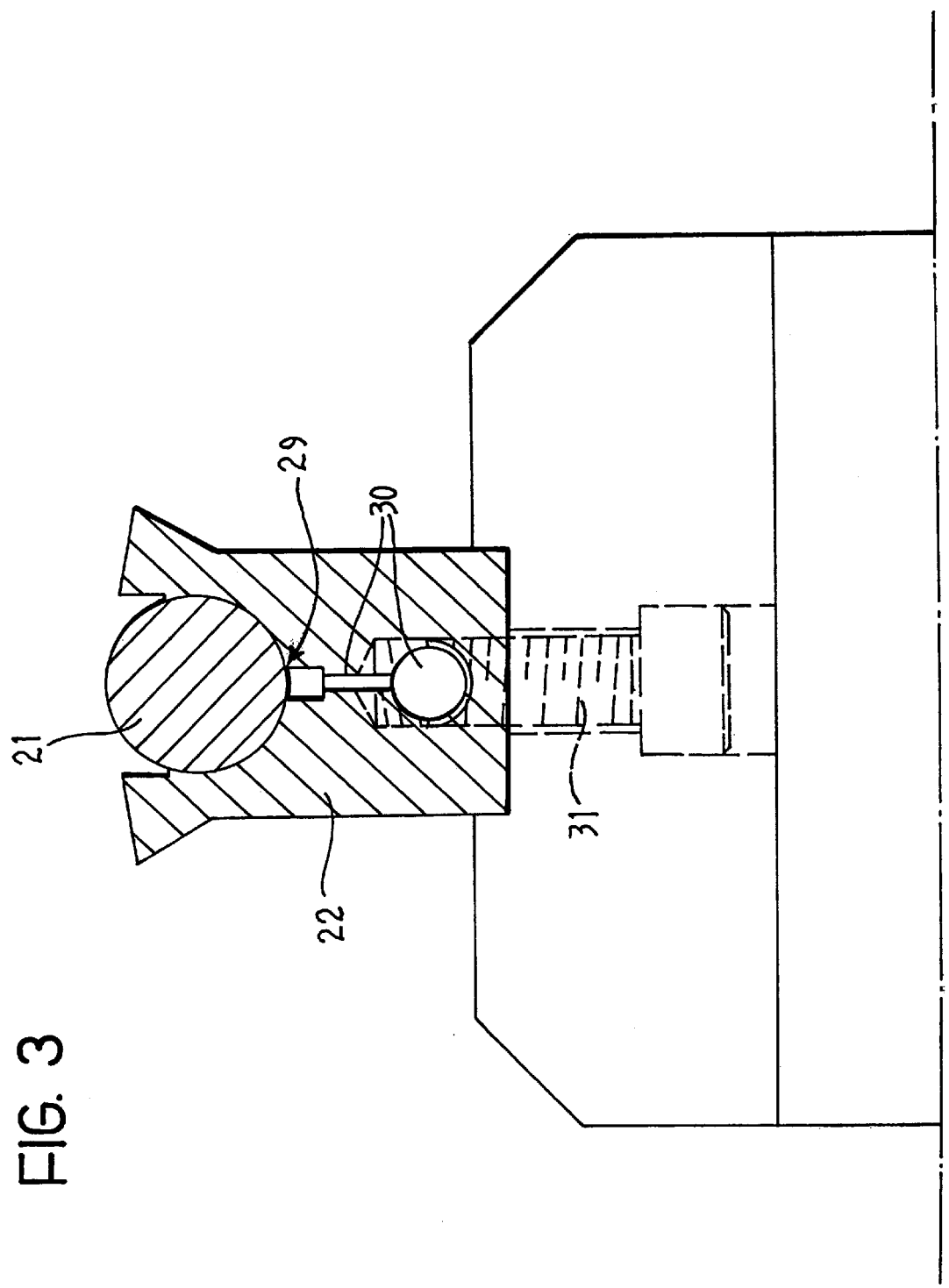

Referring now to FIG. 1, we shall suppose that the upper tract C1 of the conveyor impresses upon the articles A a motion (from the right to the left when viewing FIG. 1), with the articles moving at a speed v2.

With a view to fixing the ideas, it will be seen that the device 1 in question, complete with the series of parts that will be described in greater detail hereinbelow, realizes the operation of cutting and applying the adhesion-protection label made of siliconized paper and intended to be applied along the principal longitudinal axis of each sanitary towel A. When the sanitary towel is of the type with "wings", a series of parts substantially similar to the one described realizes the operation of cutting and applying the adhesive labels intended for application to the wings of the sanitary towel.

The material that is to constitute the adhesive-protection labels takes the form of a strip of material such as siliconized paper D that is fed to the device by a feeding or pay-out unit (not shown on the drawings). The pay-out unit is usually designed for rolls (and of a known type) and allows the strip D to move forward through a series of guide rollers, some of which are shown on the drawing, where they are indicated by the reference number 2. The strip D subsequently passes in front of an adhesive application unit, where the side of the strip D that will eventually face the sanitary towels A becomes lined at least partially with a layer of adhesive (in an intermittent manner, for example, so as to leave the actual cutting zones free of adhesive). This embodiment choice (not imperative for the purposes of realizing the invention) exploits the fact that the labels can be utilized for transferring onto the sanitary towels A the strips or formations of adhesive that these labels will be called upon to protect against exposure to the external environment until such time as the labels are removed immediately prior to the towels being used.

The regular forward motion of the strip D at a speed v1 is assured by a dragging unit that consists, at least in the embodiment example here illustrated, of a motor-operated belt conveyor 4 comprising an upstream roller 5 and a downstream roller 6 (or some equivalent return element, for example, a so-called "feather") between which there extends an active tract 7 of the belt, which has an apertured structure. The tract 7 of the belt is designed to ensure the forward motion of the strip D by virtue of exposure to a subatmospheric pressure created in a suction box (vacuum chamber) 8 located within the circuit defined by the belt 4, the active tract 7 of the belt sliding in substantially tight contact with this chamber. The aeriform pressure gradient that becomes established across the openings in the belt ensures that the strip D will remain tightly pressed against the active tract 7 and move forward with it, thus realizing the desired dragging action.

The vacuum chamber 8 is connected to an appropriate source of subatmospheric pressure, which may be—for example—a so-called vacuum pump 9. This connection is realized in a known manner through a pressure regulation unit 10. Equally well known in general (and therefore not specifically described or discussed hereinbelow,) are, for example, the specific criteria underlying the dimensioning of the belt 4 and the design of its apertured surface (generally simple circular holes) to ensure effective and regular dragging of the strip D.

Identical characteristics are presented by another belt conveyor 11 arranged in a position symmetrical with respect to the conveyor 4 (and also with respect to other elements that will be described hereinbelow). The conveyor 11 comprises a principal roller 12 with an associated return roller or feather and an active tract 14 that is exposed to the subatmosheric pressure level prevailing in a vacuum chamber 15 that is once again connected to the vacuum pump 9.

In particular, the roller 12 (which is situated at the downstream end of the active tract 14 of the conveyor 11) is provided in its interior with an appropriate depression zone (vacuum chamber) and can therefore realize—in accordance with criteria to be explained in greater detail hereinbelow—the transfer towards and onto the articles A of the labels obtained by cutting the strip D.

As already mentioned, the conveyors 4 and 11 are usually arranged in such a manner as to be specularly symmetric with respect to a notional plane α of the device 1.

In the example here illustrated the plane α is orientated in an inclined position with respect to the vertical. The strip D dragged forward by the conveyor 4—at a speed v1—thus moves downwards and onto the conveyor 11. After the strip has been subjected to a cutting action (the characteristics of which will be explained in greater detail further on), the conveyor 11 sends it, now in the form of individual labels, on its way—at a speed v2—towards the roller 12. The latter is situated in a lower position and is roughly tangential with respect to the transporting tract C1 of the conveyor C, which enables it to transfer the labels (and the layer of adhesive applied to them, whenever it is present) onto the upper face of the articles A.

In the embodiment here illustrated, where the device 1 also realizes the transfer/application of the labels onto the articles A, the operating speed of the conveyor 11 is therefore set at the value v2, which corresponds to the speed with which the articles A move forward on the conveyor C beneath it, thereby avoiding possible out-of-phase phenomena. In fact, the labels are transferred from the roller 12 (or, more precisely, from the tract of the belt 14 that at that moment is in contact with the roller 12) onto the articles A at a speed (tangential with respect to the roller 12) that corresponds exactly to the speed (linear in the example here illustrated) with which the articles A move forward on the conveyor C. This result may be obtained, and in a rather advantageous manner, by arranging things in such a way as to have the conveyor 11 controlled by (via a mechanical transmission, for example, or some electronic control unit) the so-called secondary transmission of the plant, that is to say, the driving unit that operates the conveyor C.

A coupling of this type also makes it possible to realize a situation in which the conveyor 11 will always be "in phase"

with the conveyor C, thereby ensuring that the labels obtained by cutting the strip D will be placed accurately into the desired position on the articles A.

As a general rule, the speed v1 at which the conveyor 4 obtains the strip D from the appropriate source is chosen in such a way as to have a value at least slightly smaller than the speed v2. In practice—for reasons that are wholly obvious to any expert of the sector—the ratio v2/v1 has to correspond to the ratio that exists between the "pitch" of the articles A (measured in the direction in which they move on the conveyor C) and the corresponding length L of the labels that have to be applied to the articles A.

The dragging action exerted by the conveyors 4 and 11 has to have the important characteristic of permitting the strip to slip in the longitudinal direction. This is particularly important in the case of the conveyor 11 until the moment in which the strip D fed to it from the conveyor 4 is subjected to the cutting operation, which is substantially performed in the median plane indicated by the reference letter α.

This plane, in fact, is the action site of a cutting unit that comprises a revolving knife 19 provided with several blades 20 (there are four such blades in the embodiment here illustrated) and its associated counterknife, where the latter generally consists of a cylindrical roller mounted in—but not fixed to—an appropriate reception cradle, the said roller having a very small diameter, typically of the order of 12 mm.

The revolving knife 19 consists substantially of a shaft that at its free end carries a head 24 mounted in a configuration that will enable its rotation to be controlled by a motor organ, here schematically indicated in the form of the block 26. The knife 19 may also be simply controlled (in a known manner) by the general driving unit of the machine on which the device 1 is mounted and will thus be moved directly by it.

The cutting of the strip D is realized by effect of the shearing action exerted on the strip D by the blades 20 of the knife 19 on one side and by the counter-roller 21 on the other.

As already mentioned, the roller 21, which has a very small diameter, is mounted in an appropriate reception cradle 22. With a view to avoiding—in particular— inflection and/or seizure phenomena, the roller 21 is preferably supported by an arrangement that simply provides a limited retention of the roller 21 in the cradle 22, with the contact surface of the cradle having the overall shape of a C, where the angular sweep of the said C-shaped contact surface is such as to make it terminate only barely above the semi-circumference of the roller 21. The arrangement is completed by the presence of passage or channel 29 between the surface of the cradle and the outer surface of the roller 21, the channel serving to accommodate a certain quantity of lubricating fluid that it receives via the feeding passages 30 that communicate with an appropriate supply source (not shown on the drawing), preferably at a pressure slightly above the environmental pressure. Alternative solutions may of course be employed to provide lubrication for the roller, including supporting elements made of so-called self-lubricating materials, etc.

The cradle 22 that supports the roller 21 can be mounted on the structure of the device 1 by means of—for example the interposition of screws 31. It is also possible to confer upon the cradle 22 and the roller 21 the general condition of a mounting of the floating type, for example, by means of springs intended to ensure that the roller 21 will be maintained with a limited preloading force in the position in which the said roller becomes exposed to the action of the blades 20.

Experiments carried out by the applicants have shown that the illustrated mounting condition makes it possible to operate at rather high feed rates of the strip D (300 m/min for example), cutting the siliconized paper into lengths, for example, comprised in the range between about 25 and 300 mm. To this end, the knife 19 and, more particularly, the revolving head 24 may be provided with appropriate ducts (not shown on the drawing) for feeding cooling liquid to these parts.

During the operation of the device, the strip D is fed by the conveyor 4 at a rate that is substantially equal to the speed v1 into the cutting zone, where the blades 20 come into operation. The tract of the strip that passes beyond the cutting zone is received on the conveyor 11. The latter operates at the speed v2, which is at least marginally greater than the speed v1. This difference in speed is nevertheless absorbed by the fact that the tract of the strip D (of a gradually increasing length) that extends on the conveyor 11 is capable of sliding on the surface of its active tract 14.

The gradual forward movement of the strip in the conditions that have just been described continues right up to the instant in which the tract of strip fed onto the conveyor 11 becomes of a length (measured between its free end and the section that is then located on the median plane α where the cutting unit 19, 21 operates) equal to the length it is desired to obtain by means of the cutting operation. The cutting unit 19, 21 is therefore activated at this point: the strip D is cut and the label of the predetermined length L formed in this manner is dragged forward (at the speed v2, because it is now no longer held back by the remainder of the strip D) by the conveyor 11. By means of the roller 12, on which the labels are retained owing to the presence of the vacuum chamber 12*a*, the conveyor now turns the label L upside down and applies it to an article A of the flow moving below it.

The cycle that has just been described is repeated for each label, so that a new tract of the strip D comes to be fed by the conveyor 4 across the cutting zone and gradually takes up its position on the conveyor 11; when it has attained the desired length, the cutting unit 19, 21 is again brought into action to form a new label L.

The cutting unit (in practice the knife 19) is therefore controlled with a view to the need of intervening on the strip D and cutting it at the precise moment in which the free tract of the strip that has passed beyond the cutting zone has attained the precise length desired for the labels L.

This fact (that is to say, the availability of a free tract of strip having the precise length of the label it is desired to obtain) can be detected with known means, for example, with a position sensor 5*a* associated with the roller 5 of the conveyor 4 or, more simply, by means of direct control exercised by the unit feeding the strip D and consequent detection of the moment at which the said unit, following the last cutting operation, has fed a tract of strip having a length equal to the desired length to which the labels are to be cut. The necessary information can be sent to the general control unit that supervises the operation of the knife 19.

This unit, here schematically presented by the block K, may consist of an appropriate processing system or, more simply, of an appropriate set of processing resources assigned within the ambit of the processing unit that supervises the automatic operation of the plant in which the device 1 is incorporated or, in an even simpler manner, of control exercised albeit with appropriate phasing—by the other mobile organs of the device.

The solution according to the invention is therefore capable of adapting itself to the length variations of the labels L and/or the articles A, and this particularly when it is desired to realize a so-called "format change".

To obtain the proper functioning of the device 1 it is sufficient to ensure exact regulation of the parameters relating to the speed v1 (which in most cases is obtained automatically due to overall control by the secondary driving unit of the plant as previously described), the speed v2 (consequence of the length of the labels L it is desired to apply and function of the feed rate of the articles A) and the instant at which the knife 19 is to intervene (so as to obtain the precise phasing of the cutting operation, also as a function—where appropriate—of the subsequent application operation).

It will also be readily appreciated that the solution according to the invention is not in any way dependent on the use of a knife 19 of the revolving type with an associated counter-roller like the counter-roller 21 of the type described hereinabove. Though this solution is undoubtedly the one to be preferred (not least as regards the characteristics of the counter-roller 21), the previously described function of cutting the labels to length could also be carried out with a cutting organ of a different type, for examples with a knife performing a reciprocating motion (of the knife/anvil type and a rectilinear approach and retraction movement) and/or a thermal cutting organ (hot wire cutting device, laser beam cutter, etc.). In fact, the choice of the cutting organ is subject to the one and only requirement of realizing a duly phased procedure for cutting the strip D into pieces that will all have the length of the label L it is desired to apply to the articles.

The preceding remarks also bring out the fact that, even though the embodiment example of the invention here illustrated envisages that the conveyor 5 (which acts as feeder of the strip D) and the conveyor 11 (which acts as the organ receiving the strip D and the labels L) are configured in such a way that the slip of the strip D prior to its being cut by the knife 19 should occur primarily relative to the reception conveyor 11, one can also envisage other realization variants in which the slip (needed in order to compensate the difference between the speeds v1 and v2) is obtained (also) relative to the feed conveyor 4.

Without prejudice to the principle of the invention, of course, the realization details and the embodiments can be very extensively varied with respect to what has been described and illustrated hereinabove without in any way going beyond the ambit of the invention as set out in the claims attached hereto.

What is claimed is:

1. A device for cutting laminar elements to a predetermined length, including:

feeding means capable of feeding a strip for formation of said laminar elements;

reception means capable of receiving said strip and said laminar elements formed from said feeding means; and cutting means interposed between said feeding means and said reception means, where said cutting means is selectively controlled to cut said strip at points where a paid out length of the strip corresponds to said predetermined length, and wherein said feeding means pays out said strip at an appropriate first speed and said reception means acts on said strip at an appropriate second speed, said second speed being greater than said first speed, and wherein at least one of said feeding means and said reception means is configured to permit the strip to slip;

wherein said feeding means is associated with a sensor means and a control means, said sensor means being capable of detecting an amount of said strip that has been paid out by said feeding means and providing an input representing the detected amount of said strip to said control means, and wherein said cutting means is operated by said control means when the detected amount of said strip substantially equals said predetermined length.

2. The device of claim 1 in combination with conveyor means for transporting at a given speed having articles intended to receive said laminar elements, wherein said reception means has a dragging action controlled by said conveyor means, so that said reception means becomes capable of feeding said laminar elements to the articles present on said conveyor means at a rate substantially the same as said given speed at which the articles are being transported.

3. The device of claim 1, wherein said feeding means and said reception means are configured to ensure that the slip of the strip will be realized primarily between said feeding means and the said reception means.

4. The device of claim 1, wherein said cutting means includes a revolving knife.

5. The device of claim 4, wherein said revolving knife includes a plurality of blades mounted in accordance with a general carousel configuration on a body of the revolving knife.

6. The device of claim 1, wherein said feeding means includes a belt conveyor.

7. The device of claim 6, wherein said belt conveyor includes retention means capable of acting on said strip by virtue of a pressure gradient.

8. The device of claim 7, wherein said belt conveyor has associated with it an aeriform pressure means capable of acting on an active tract in such a way as to create at said active tract a pressure gradient that will keep the strip in contact with said active tract.

9. The device of claim 8, wherein said aeriform pressure means includes a chamber with associated means for applying a subatmospheric pressure level to an inside of the chamber and wherein said belt conveyor is an apertured belt.

10. The device of claim 1, wherein said reception means includes a respective belt conveyor.

11. The device of claim 6, wherein said reception means includes a respective retention means capable of acting on said strip by virtue of a pressure gradient.

12. The device of claim 11, wherein said reception means has associated with it an aeriform pressure means capable of acting on an active tract of said reception means to create at said active tract, a pressure gradient that maintains said strip in contact with said reception means.

13. The device of claim 12, wherein said aeriform pressure means includes a chamber with an associated means for applying a subatmospheric pressure level to an inside of the chamber and wherein said belt conveyor is an apertured belt.

14. The device of claim 11 in combination with conveyor means for transporting at a given speed, having articles intended to receive said laminar elements, wherein said reception means has a dragging action controlled by said conveyor means, so that said reception means becomes capable of feeding said laminar elements to the articles present on said conveyor means at a rate substantially the same as said given speed at which the articles are being transported and wherein the said respective belt conveyor includes a terminal tract that operates to transfer said laminar elements onto said articles.

15. The device of claim 1, wherein said cutting means includes a counterknife element capable of cooperating with at least one blade element for cutting the strip to realize said elements.

16. The device of claim 15, wherein the counterknife element consists of a supported revolving body, which allows it to revolve freely.

17. The device of claim 15, wherein said counterknife element has associated with it elastic means for exerting an elastic load on the counterknife element in the direction of the strip.

18. The device of claim 15, wherein said counterknife element is supported in a respective reception cradle.

19. The device of claim 18, wherein said reception cradle is provided with cavities for a mass that will exert an antagonistic action as far as friction is concerned.

20. The device of claim 15, wherein said counterknife element is configured as a roller.

21. The device of claim 20, wherein said roller has a generally elongated configuration.

22. The device of claim 20, wherein said roller has a diameter of about 12 mm.

* * * * *